United States Patent [19]

Morgan

[11] 4,178,371
[45] Dec. 11, 1979

[54] TETRAPEPTIDE DERIVATIVES

[75] Inventor: Barry A. Morgan, Hessle, England

[73] Assignee: Reckitt & Colman Products Limited, London, England

[21] Appl. No.: 964,074

[22] Filed: Nov. 27, 1978

[30] Foreign Application Priority Data

Dec. 15, 1977 [GB] United Kingdom ............... 52237/77
Apr. 8, 1978 [GB] United Kingdom ............... 13845/78

[51] Int. Cl.² ..................... A61K 37/00; C07C 103/52
[52] U.S. Cl. ............................... 424/177; 260/112.5 R
[58] Field of Search ................... 424/177; 260/112.5 R

[56] References Cited

PUBLICATIONS

Yamashiro, et al., Biochem. and Biophys. Res. Commun., 78, 1977, pp. 1124–1129.

Primary Examiner—Delbert R. Phillips
Attorney, Agent, or Firm—Bacon & Thomas

[57] ABSTRACT

Tetrapeptide amides of the formula

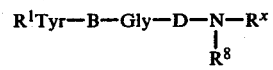

wherein $R^1$, $R^8$, $R^x$, B and D represent certain specified substituent groups. The compounds exhibit pharmacological activity when tested in vitro in the transmurally stimulated guinea pig ileum preparation indicating their affinity for opiate receptor sites, and also in vivo tests, with intravenous administration, indicating their analgesic effects, and hence their utility as analgesic agents.

14 Claims, No Drawings

TETRAPEPTIDE DERIVATIVES

This invention relates to peptides, to processes for their preparation and to therapeutic compositions thereof.

According to this invention there are provided compounds of the formula:

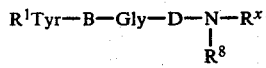

wherein $R^1$ is hydrogen, methyl, allyl, dimethylallyl, propargyl, cyclopropylmethyl, cyclobutylmethyl or phenethyl;

B is the group

—NH—CR$^3$H—CO— in which $R^3$ is alkyl $C_{1-6}$ or $C_qH_{2q}YC_rH_{2r+1}$ (where q is 1-2, r is 0-1 and Y is O, S, SO or $SO_2$);
the group having the D-configuration;
D is the group

—NR$^5$—CR$^6$H—CO— in which
$R^5$ is hydrogen or methyl;
$R^6$ is Ar-alkyl $C_{1-3}$;
the group having the L-configuration;
$R^8$ is hydrogen, alkyl $C_{1-5}$, Ar or Ar-alkyl $C_{1-2}$;
$R^x$ is a group $(CH_2)_s$—X where s is 2-4 and X is NHR$^9$, N$^\oplus$R$^{11}$R$^{12}$R$^{13}$, NR$^9$COR$^{11}$, NR$^9$COOR$^{11}$, NR$^9$CONH$_2$, NR$^9$CONR$^{10}$R$^{11}$, N(O)$_n$R$^{11}$R$^{12}$, COOR$^9$, CONR$^9$R$^{10}$, or OCONR$^9$R$^{10}$ (where $R^9$ is hydrogen, alkyl $C_{1-3}$, Ar or ArCH$_2$;
$R^{10}$ is hydrogen or alkyl $C_{1-3}$; $R^{11}$ is alkyl $C_{1-3}$, Ar or ArCH$_2$; $R^{12}$ is alkyl $C_{1-3}$; $R^{13}$ is alkyl $C_{1-3}$;
and n is 0 or 1);
or the group

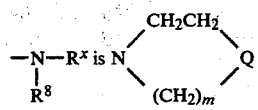

where m is 1-3 and Q is SO, $SO_2$, CO, CHOH, N$^\oplus$MeR$^{11}$ or N(O)R$^{11}$;

Ar is phenyl or phenyl substituted by chlorine, methyl, hydroxy or methoxy; and their acid addition salts.

Examples of B include D-alanine, D-α-aminobutyric acid, D-valine, D-norvaline, D-leucine, D-norleucine, D-serine, D-threonine, D-methionine and D-methionine sulphoxide.

Examples of D include L-phenylalanine and N-methyl-L-phenylalanine.

In an aspect of the invention there are provided compounds of Formula I wherein $R^1$ is hydrogen, methyl, allyl, dimethylallyl, propargyl, cyclopropylmethyl, cyclobutylmethyl or phenethyl;

B is the group

—NH—CR$^3$H—CO— in which $R^3$ is alkyl $C_{1-6}$ or $C_qH_{2q}YC_rH_{2r+1}$ (where q is 1-2, r is 0-1 and Y is O, S, SO or $SO_2$), the group having the D-configuration;
D is the group

—NR$^5$—CR$^6$H—CO— in which
$R^5$ is hydrogen or methyl;
$R^6$ is Ar-alkyl $C_{1-3}$, the group having the L-configuration;
$R^8$ is hydrogen or alkyl $C_{1-5}$;
$R^x$ is a group $(CH_2)_s$—X where s is 2-4 and X is NHR$^9$, NR$^9$COR$^{11}$, NR$^9$CONH$_2$, NR$^9$CONR$^{10}$R$^{11}$, N(O)$_n$R$^{11}$R$^{12}$, COOR$^9$, CONR$^9$R$^{10}$, NR$^9$COOR$^{11}$ or OCONR$^9$R$^{10}$ (where $R^9$ is hydrogen or alkyl $C_{1-3}$; $R^{10}$ is hydrogen or alkyl $C_{1-3}$; $R^{11}$ is alkyl $C_{1-3}$; $R^{12}$ is alkyl $C_{1-3}$ and n is 0 or 1);

Ar is phenyl or phenyl substituted by chlorine, methyl, hydroxy or methoxy; and their acid addition salts.

The symbols used herein for amino-acid derivatives are those customarily used in peptide chemistry such as are set out in Biochem. J. 126. 773 (1972). All amino-acid residues are of the natural or L-configuration unless specified otherwise.

The invention also provides therapeutic compositions comprising a compound of the formula, or a pharmaceutically acceptable acid addition salt thereof, in association with a pharmaceutically acceptable diluent or carrier. Suitable salts are the hydrochlorides, phosphates, citrates and acetates.

The compounds of the invention exhibit pharmacological activity. Thus for example, by in vitro testing they have been found to have affinity for opiate receptor sites and as such may be used as analgesics, narcotic antagonists or anti-diarrhoeal agents. The test used for the detection of their agonist activity at opiate receptor sites is that employing the transmurally stimulates guinea pig ileum preparation described in Kosterlitz et al., Brit. J. Pharmacol, and Chemotherapy 33. 266–276 (1968). They have also been shown to exhibit analgesic activity when tested in vivo for example in the mouse phenyl-quinone anti writhing test of Hendershot et al., J. Pharmac. Exp. Ther. 125, 237 (1959) and by the rat tail flick test (intravenous administration) according to Jansen et al., Arzneim Forsch. 13, 266 (1963).

The Compounds of the invention may be prepared by the standard methods of peptide chemistry.

Thus they may be produced by sequential coupling, of suitably protected and activated amino acids by either classical solution methods or solid phase procedures, or by coupling fragments consisting of suitably protected peptides.

Details concerning the selection of protecting groups and methods for their incorporation as well as suitable reaction conditions for forming amido (peptide) linkages and removal of protecting groups may be found in the following references:

(a) Houben Weyl; Methoden der Organischen Chemie Vol. 16; Parts I and II Syntheses von Peptiden (Thieme 1974).

(b) Schroder & Lubke "The Peptides"; Academic Press (1965).

Thus the compounds of formula I may be prepared by condensing a compound of formula II $$Y-M_1-OH \qquad \qquad II$$

where Y is a suitable N-protecting group and $M_1$ is a suitably protected amino acid or peptide residue, with a compound of formula III $$H-M_2-N-R^x \qquad \qquad III$$
$$\quad\quad\quad |$$
$$\quad\quad\quad R^8$$

where $M_2$ is a suitably protected amino acid or peptide residue (where $M_1$ and $M_2$ together represent —Tyr—B—Gly—D— or a protected derivative thereof), followed by removal of the protection.

The coupling of II and III may be achieved by the standard methods of peptide synthesis, either with or without isolation of the activated component corresponding to the compound of formula II. Conveniently a protected N-terminal dipeptide is coupled with a C-terminal dipeptide amide or a protected N-terminal tripeptide is coupled with a C-terminal amino acid amide followed in either case by the removal of the protection.

A useful NH-protecting group is t-butyloxy carbonyl and a particularly useful OH protecting group is the t-butyl radical both of which may be removed by treatment of the protected compound with hydrogen chloride in a solvent such as ethyl acetate or acetic acid or with trifluoroacetic acid.

The compounds of Formula I in which B is a group —NH—$CR^3$H—CO— where $R^3$ is $C_qH_{2q}YC_rH_{2r+1}$ and in which Y is SO or $SO_2$ may be prepared from the analogous compounds in which Y is S by oxidation with for example hydrogen peroxide in a solvent such as acetic acid or methanol. They may also be prepared by carrying out the oxidation on a protected compound of formula I followed by deprotection.

The compounds of Formula I in which $R^x$ is $(CH_2)_s$—X and X is $N(O)R^{11}R^{12}$ may also be prepared from the analogous compounds in which X is $NR^{11}R^{12}$ by oxidation with for example hydrogen peroxide in a solvent such acetic acid or methanol, or by oxidation with meta-chloroperbenzoic acid. This method of oxidation is also applicable for the preparation of intermediate amino acid amides or dipeptide amides containing the group $N(O)R^{11}R^{12}$.

The compounds of Formula I in which the group $$-N-R^x \text{ is } N \begin{array}{c} CH_2CH_2 \\ \diagup \quad \diagdown \\ \quad\quad Q \\ \diagdown \quad \diagup \\ (CH_2)_m \end{array}$$
$$\;|$$
$$R^8$$

and where Q is $N(O)R^{11}$, SO or $SO_2$ may be prepared from the analogous compounds where Q is $NR^{11}$ or S respectively by similar methods of oxidation. Intermediate amino acid amides or dipeptide amides containing these groups may be prepared in an analogous manner.

The invention is illustrated by the following non-limiting Examples in which temperatures are in degrees Celsius.

The following abbreviatives are used throughout
BOC: t-Butyloxycarbonyl
$Bu^t$: t-Butyl
IBCF: Isobutylchloroformate
Z: Benzyloxycarbonyl
DCCI: Dicyclohexylcarbodiimide
DCU: Dicyclohexylurea
HONSu: N-Hydroxysuccinimide
NMM: N-Methylmorpholine
DMF: Dimethylformamide
DME: 1,2-Dimethoxyethane
THF: Tetrahydrofuran The various compounds and intermediates were examined by thin layer chromatography (t.l.c.) on silica gel plates (Kieselgel $GF_{254}$) using the following systems:
1E methanol, chloroform—1:2
1F methanol, chloroform—1:19
2B chloroform, methanol, acetic acid—19:9:1
3A chloroform, methanol, acetic acid, water—60:18:2:3
3B chloroform, methanol, acetic acid, water—30:18:4:6
3C chloroform, methanol, acetic acid, water—90:27:2:3
3D chloroform, methanol, acetic acid, water—30:20:2:3
4A isobutanol, ethyl acetate, acetic acid, water—1:1:1:1
5B isobutanol, acetic acid, water—3:1:1
7B ethylacetate, pyridine, acetic acid, water—60:20:6:11
7C ethylacetate, pyridine, acetic acid, water—120:20:6:11
7D ethylacetate, pyridine, acetic acid, water—240:20:6:11
7F ethylacetate, pyridine, acetic acid, water—480:20:6:11
8A chloroform, isopropanol—3:1
8B chloroform, isopropanol—9:1

EXAMPLE 1

L-Tyrosyl-D-alanylglycyl-L-phenylalanin-2-acetamidoethylamide

This was prepared according to the following method

| Tyr | D-Ala | Gly | Phe | |
|---|---|---|---|---|
| | | BOC— | —OH | $NH_2CH_2CH_2NHCOCH_3$ |
| | $Bu^t$ | BOC— | | —$NHCH_2CH_2NHCOOCH_3$ |
| BOC— | $Bu^t$ | —OH $Cl^\ominus H_2^\oplus$— | | —$NHCH_2CH_2NHCOCH_3$ |
| BOC— | | | | —$NHCH_2CH_2NHCOCH_3$ |
| H— | | | | —$NHCH_2CH_2NHCOCH_3$ |

(1) BOC—Phe—NH $CH_2CH_2NHCOCH_3$

BOC—Phe—OH (2.65 g) was dissolved in $CH_2Cl_2$ (20 ml) and the solution cooled to −20° when NMM (1.01 g) and IBCF (1.37 g) were added followed by $H_2NCH_2CH_2NH.COCH_3$ (1.2 g) after 2 minutes. The reaction mixture was allowed to attain room temperature and stirred for 21 hours when the solvent was evaporated and the gum dissolved in chloroform. The solution was washed with a saturated solution of NaHCO₃, 10% aqueous citric acid, with water until neutral and finally with a saturated brine solution. The organic phase was dried (Na₂SO₄) and evaporated to a solid which crystallised from ethyl acetate to yield the amide 1 (3.0 g). Rf 7F 0.35.

(2) Cl⁻H⁺Phe—NHCH₂CH₂NHCOCH₃

BOC—Phe—NHCH₂CH₂NHCOCH₃ (3 g) was dissolved in 5 M HCl in ethyl acetate (20 ml) and 2.6 M HCl in acetic acid (5 ml), and stirred at ambient temperature for 30 minutes. The solvent was evaporated and the residue triturated several times with dry dithyl ether. The hydrochloride (2) was obtained as a hygroscopic solid (0.45 g) Rf3B 0.5

(4) BOC—Gly—Phe NHCH₂CH₂NHCOCH₃

This was prepared by either of the following approaches:

(a) BOC-Gly-Phe-OH (1.0 g) and H₂NCH₂CH₂NHCOCH₃ (0.4 g) were dissolved in DMF and cooled in an ice/salt bath where HONSu (0.78 g) and DCCI (0.668 g) were added. The reaction mixture was allowed to attain room temperature and stirred overnight when the DCU was removed by filtration and the solvent evaporated. The residue was dissolved in CHCl₃, washed with saturated sodium bicarbonate solution (2×50 ml), 10% aqueous citric acid (2×50 ml) and water until neutral, and then with a saturated brine solution. The organic phase was dried (Na₂SO₄) and evaporated. The residue was chromatographed on a silica gel column (45 cm×2.4 cm). The column was first eluted with CHCl₃/isopropanol (19:1) then with CHCl₃/isopropanol (4:1). The title compound was obtained as a gum (0.60 g) Rf8B 0.4, Rf7F 0.2.

(b) BOC—Gly—OH (1.072 g) was dissolved in CH₂Cl₂ and cooled in solid CO₂/CCl₄ bath when NMM (0.618 g) and IBCF (0.836 g) were added. After 2 minutes at this temperature Cl⁻H⁺.Phe-NHCH₂CH₂NHCOCH₃ (1.75 g) and NMM (0.618) were added and the temperature allowed to rise to room temperature. The reaction was worked up after overnight stirring as described for (1) above. The residue was purified according to (a) above. The product was obtained as a gum (0.65 g). Rf8B 0.4, Rf7F 0.2.

(5) BOC-Tyr(Buᵗ)—D—Ala—Gly—Phe—NHCH₂CH₂NHCOCH₃

(i) BOC—Gly—Phe—NHCH₂CH₂NHCOCH₃ (0.64 g) was treated with 5.5 M HCl in ethyl acetate (5 ml) and 2.6 M HCl in acetic acid (5 ml) at ambient temperature. After 45 minutes the solvent was evaporated and the residue triturated with diethyl ether. The dipeptide hydrochloride was obtained as a hygroscopic solid (0.54 g) Rf 3D 0.45.

(ii) BOC—Tyr(Buᵗ)—D—Ala—OH (0.6 g) and Cl⁻H⁺Gly-Phe-NHCH₂CH₂NHCOCH₃ (0.5 g) were dissolved in DMF (3 ml) and cooled in ice/salt bath when HONSu (0.355 g) and DCCI (0.303 g) were added followed by NMM (1.48 g in DMF, 1.5 ml). The reaction mixture was allowed to warm up to room temperature and stirred overnight. DCU was then filtered off, the solvent evaporated and the residue partitioned between ethyl acetate and water. The organic layer was washed with a saturated aqueous sodium bicarbonate solution (2×50 ml), 10% aqueous citric acid (2×50 ml), water until neutral, and finally with saturated brine solution. The organic phase was dried (Na₂SO₄) and evaporated. The tetrapeptide was obtained as a gum (0.65 g). Rf7C 0.65 Rf3D 0.8.

(6)
H—Tyr—D—Ala—Gly—Phe—NHCH₂CH₂NH-COCH₃

BOC-Tyr(Buᵗ)—D—Ala—Gly—Phe—NHCH₂CH₂NHCOCH₃ (0.65 g) was treated with excess 2.6 M HCl in acetic acid for 45 minutes at ambient temperature. The solvent was evaporated and the residue chromatographed on a silica gel column (50 cm×2.5 cm) with solvent system 3A. The resultant gum was lyophilised to yield the title compound (0.45 g) Rf3A 0.3 [α]_D^{22} −6.95° (c=1, DMF).

EXAMPLE 2

L-Tyrosyl-D-alanylglycyl-N-methyl-L-phenylalanine-3-dimethylaminopropylamide

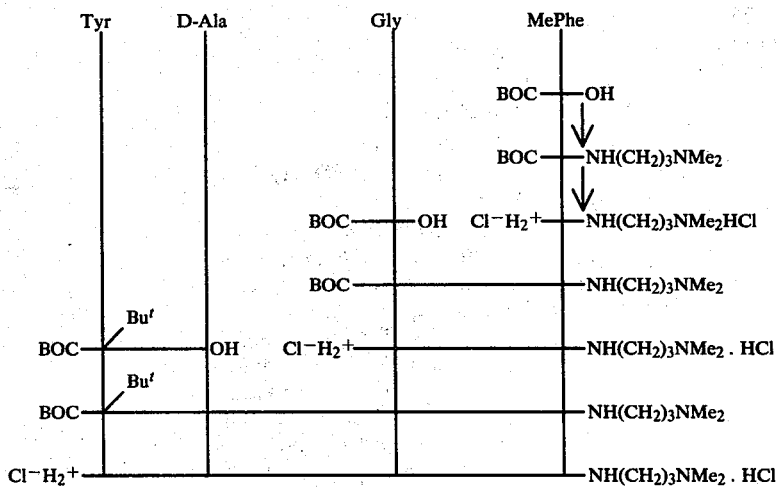

This was prepared by the method of the above scheme:

(1) BOC-MePhe-NHCH₂CH₂CH₂NMe₂

N-t-Butyloxycarbonyl-N-methylphenylalanine (2.79 g) and NMM (1.01 g) were dissolved in dichloromethane (20 ml) and the stirred solution cooled to −20°. IBCF (1.37 g) was then added and the mixture stirred for 5 minutes before the addition of NH₂CH₂CH₂CH₂NMe₂ (1.02 g). The solution was stirred for 1 hour at −20° and then at room temperature for 12 hours. The mixture was evaporated, and the residue dissolved in ethyl acetate (50 ml) and an aqueous solution of sodium bicarbonate (saturated, 50 ml). The ethyl acetate layer was washed with aqueous sodium bicarbonate (saturated, 50 ml), water (2×50 ml) and 10% aqueous citric acid (2×50 ml). The citric acid extracts were combined, made basic with saturated sodium bicarbonate solution, and extracted with ethyl acetate (3×50 ml). The ethyl acetate extracts were combined, dried (Na₂SO₄) and evaporated to yield the title compound as an oil Rf1E 0.24, Rf3A 0.37.

(2) H—MePhe—NHCH₂CH₂CH₂NMe₂.2HCl

The oil from (1) above was dissolved in ethyl acetate (10 ml), and HCl in acetic acid (2.63M, 6 ml) and HCl in ethyl acetate (5.7 M, 6 ml) added. The solution was stirred for 2 hours and evaporated to yield the desired dihydrochloride salt (2.2 g) as a solid Rf1E 0.02, Rf3A 0.03.

(3) BOC—Gly—MePhe—NHCH₂CH₂CH₂NMe₂ t-Butyloxycarbonylglycine (1.05 g) and NMM (0.606 g) were dissolved in dichloromethane (12 ml) and the stirred solution cooled to −20°. IBCF (0.819 g, 6mM) was added and the mixture stirred for 5 minutes before the addition of (2) above (2.02 g) in DMF (5 ml). The solution was stirred for 1 hour at −20° and 12 hours at room temperature and then evaporated. The residue was dissolved in ethyl acetate (50 ml) and an aqueous solution of sodium bicarbonate (10% 50ml). The organic phase was separated, washed with aqueous sodium bicarbonate (10% 3,×50 ml) and water (3×50 ml). The ethyl acetate solution was dried (Na₂SO₄) and evaporated to yield the title compound as an oil. Rf1E 0.21; Rf3A 0.37.

(4) H—Gly—MePhe—NHCH₂CH₂CH₂NMe₂.2HCl

The protected dipeptide (3) was treated by the procedure as described for (2) above to yield the desired dihydrochloride salt (4) (2.0 g) as a white solid. Rf1E 0.03, Rf3A 0.03.

(5)
BOC—Tyr(Buᵗ)—D—Ala—Gly—Me-
Phe—NHCH₂CH₂CH₂NMe₂

BOC—Tyr(Buᵗ)—D—Ala—OH (1.22 g), H—Gly—MePhe—NHCH₂CH₂CH₂NMe₂.2HCl (1.18 g), HONSu (0.345 g) and NMM (0.30 g) were dissolved in dry DMF (20 ml) and the solution cooled to 0°. DCCI (0.680 g) was added and the mixture stirred for 18 hours before evaporation. The residue was dissolved in ethyl acetate (50 ml) and washed with aqueous sodium bicarbonate (10%, 2×50 ml), water (2×50 ml), dried (Na₂SO₄) and evaporated to dryness. The residue was dissolved in methanol, applied on a column of silica gel (35×2 cm) and eluted with solvent system 1F. The fractions containing the desired compound were bulked, evaporated, and the residue dissolved in ethyl acetate (100 ml). The ethyl acetate extracts were washed with aqueous sodium bicarbonate (10%, 3×100 ml), dried and evaporated to yield the title compound tetrapeptide (5) as a white solid Rf1E 0.18, Rf3A 0.39.

(6)
H—Tyr—D—Ala—Gly—MePhe—NHCH₂CH₂CH₂-
NMe₂

The protected tetrapeptide (5) (500 mg) was dissolved in ethyl acetate (5 ml) and a solution of hydrogen chloride in ethyl acetate (5.7 M, 2.5 ml) added to the stirred solution. After 1 hour, the reaction mixture was filtered and the residue washed with petrol ether, dried and lyophilised from water to yield the product (380 mg) as a white solid. Rf4A 0.27, Rf3B 0.47, [α]₅₇₈²²+23.6 (c=1; 0.1M HCl).

EXAMPLE 3

L-Tyrosyl-D-alanylglycyl-N-methyl-L-phenylalanine-
2-dimethylaminopropylamide-N-oxide (1)
BOC—Tyr(Buᵗ)—D—Ala—Gly—Me-
Phe—NHCH₂CH₂CH₂N(O)Me₂

BOC—Tyr(Buᵗ)—D—Ala—Gly—Me-
Phe—NHCH₂CH₂CH₂NMe₂ (500 mg) was dissolved in methanol (10 ml) and an aqueous solution of hydrogen peroxide (30%, 0.16 ml) added. The solution was stirred for 48 hours at room temperature, filtered and evaporated to yield the desired protected N-oxide as a gum. Rf1E 0.08; Rf3A 0.41.

(2)
H—Tyr—D—Ala—Gly—MePhe—NHCH₂CH₂CH₂-
N(O)Me₂

The gum from (1) above was dissolved in ethyl acetate (5 ml) and a solution of HCl in ethyl acetate (2.63 M, 1 ml) added. The solution was stirred for 1 hour, filtered, the solid dried and lyophilised from water to yield the desired product (240 mg) as a white solid. Rf4A 0.56; Rf3B 0.52 [α]₅₇₈²²=+18.8° (c=1; 0.1M HCl).

EXAMPLE 4

L-Tyrosyl-D-alanylglycyl-N-methyl-L-phenylalanine-
2-dimethylaminoethylamide

This was prepared according to the following method:

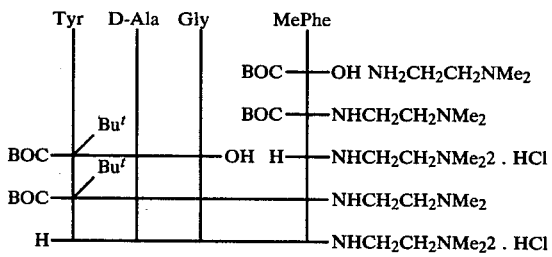

(1) BOC—MePhe—NHCH₂CH₂NMe₂

BOC—MePhe—OH and N,N-dimethylethylenediamine are coupled by the procedure of Example 1(1) to yield the desired amide as an oil.

(2) HMePhe—NHCH₂CH₂NMe₂.2HCl

The N-protected amide from (1) above was deprotected by the method of Example 1(2) to yield the desired hydrochloride salt as an oil.

(3)

BOC—Tyr—(Bu$^t$)—D—Ala—Gly—Me-
Phe—NHCH$_2$CH$_2$NMe$_2$

BOC—Tyr—(Bu$^t$)—D—Ala—Gly—OH (700 mg, 1.5 mM) was dissolved in dry DMF (7.5 ml) and NMM (152 mg, 1.5 mM) added. The stirred solution was cooled to −15° and IBCF (205 mg, 1.5 mM) added. After 5 minutes a solution of 2HCl.H—Me-Phe—NHCH$_2$CH$_2$NMe$_2$ (568 mg, 1.5 mM) was added followed by NMM (303 mg, 3 mM). After 18 hours the reaction mixture was evaporated, and the residue partitioned between EtOAc (50 ml) and saturated aqueous sodium bicarbonate solution (50 ml). The ethyl acetate layer was separated, washed with saturated aqueous sodium bicarbonate solution (50 ml), water (2×50 ml) and brine (50 ml), dried (Na$_2$SO$_4$) and evaporated. The residue was chromatographed on silica gel using solvent system 7B. Appropriate fractions were pooled and evaporated to yield the desired tetrapeptide amide (700 mg) as a glassy solid.

(4)

2HCl.H—Tyr—D—Ala—Gly—Me-
Phe—NHCH$_2$CH$_2$NMe$_2$

The protected peptide from (3) was deprotected by the method of example 2(6) to yield the desired product. After lyophilsation the tetrapeptide amide (200 mg) was obtained as a white solid. Rf7B 0.04, Rf3A 0.07, Rf4A 0.23 $[\alpha]_D^{20} = -24.2°$ (c=0.50, DMF).

EXAMPLE 5

L-Tyrosyl-D-alanylglycyl-L-phenylalaninethiomorpholineamide-S-oxide

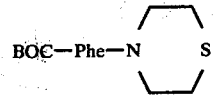
(1)

BOC—Phe—OH (1.32 g) and IBCF (680 mg) in DME (10 ml) were cooled to −20° and NMM (520 mg) was added to the stirred and cooled solution. After 2 minutes a cold suspension of thiamorpholine hydrochloride (690 mg) and NMM (520 mg) in DMF (8 ml) was added. Stirring was continued for 30 minutes at −20° and then at room temperature overnight. After evaporation of the solvent the resulting material was partitioned between ethyl acetate and saturated aqueous sodium bicarbonate solution. The ethyl acetate layer was extracted three times with saturated sodium bicarbonate solution, twice with 10% solution of citric acid in water, and then with water, and finally with saturated sodium chloride solution. The ethyl acetate solution was dried (Na$_2$SO$_4$) and evaporated to give the thiamorpholineamide as a gum (1.56 g).

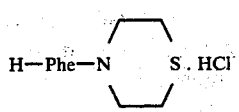
(2)

A stirred solution of

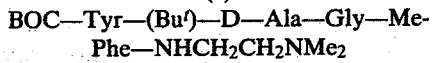

(1.05 g) in acetic acid (3 ml) was treated at room temperature with a solution of hydrogen chloride in acetic acid (2.6 M, 3 ml), and at two-hourly intervals, with two further 3 ml portions. After evaporation of the solvent and hydrogen chloride, the residue was rubbed with dry diethyl ether, the ether decanted and the residue rubbed with fresh dry ether to give phenylalanine thiamorpholine amide as a solid (738 mg).

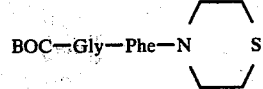
(3)

BOC—Gly—OH (384 mg) was coupled to

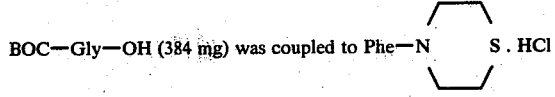

(572 mg) by the method used above for

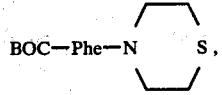

with the use of IBCF (258 mg) and NMM (424 mg total). 774 mg of dipeptide amide was obtained.

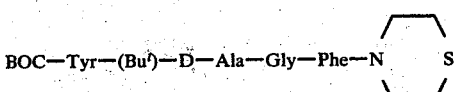
(4)

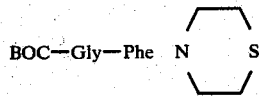

(697 mg) was stirred with aqueous trifluoroacetic acid (H$_2$O:CF$_3$CO$_2$H 1:9 9ml) for 1½ hours. The acid was evaporated and the residue was triturated with diethyl ether to give a powder which was dissolved in dry DMF (5 ml) and adjusted with NMM to pH 8 (moist indicator paper). BOC—Tyr—(Bu$^t$)—D—Ala—OH (680 mg) and HONSu (211 mg) in DMF (3 ml) were added followed by DCCI (377 mg) and the mixture stirred overnight at room temperature. The solid was removed by filtration and the filtrate was evaporated to a gum which was partitioned between ethyl acetate and saturated aqueous sodium bicarbonate solution. The ethyl acetate layer was washed twice with saturated aqueous sodium bicarbonate solution then three times with 10% citric acid in water, then with water and saturated sodium chloride solution. Drying (Na$_2$SO$_4$)

and evaporation gave the protected tetrapeptide thiamorpholine amide (1.09 g).

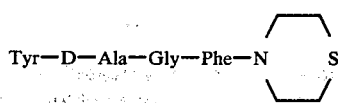
(5)

The protected tetrapeptide thiamorpholine amide (1.0 g) was stirred in aqueous trifluoroacetic acid ($H_2O:CF_3CO_2H$ 1:9, 9ml) for 1½ hours. Evaporation and trituration with diethyl ether gave a solid which was purified by chromatography on silica gel ($CHCl_3:CH_3OH:AcOH:H_2O$ 60:18:1:1.5) and then by ion exchange chromatography (Sephadex SP resin, pyridinium form, using a gradient from 2% pyridine in water to 5% pyridine, 1% acetic acid in water). The product was lyophilised to give the tetrapeptide thiomorpholine amide (495 mg).

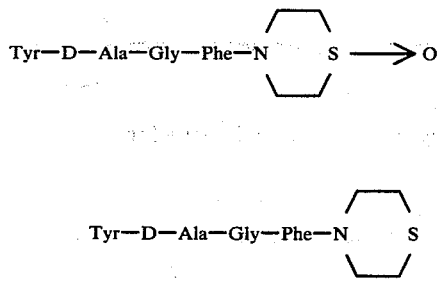
(6)

(100 mg) in ethanol (50 ml) was treated with three successive portions of 20 volume hydrogen peroxide (0.3 ml each) at intervals of 45 mins. with stirring at room temperature. After further stirring for 1 hour the solution was evaporated to dryness, dissolved in water (20 ml) and lyophilised to give a white solid (98 mg). Rf3A 0.25; Rf7C 0.06; Rf5B 0.38 $[\alpha]_{589}^{18.5} = +53.1°$ (c=0.47, in 0.1 N HCl).

EXAMPLE 6

L-Tyrosyl-D-alanylglycyl-N-methyl-L-phenylalanine-2-aminoethylamide

Tyr—D—Ala—Gly—MePhe—NHCH₂CH₂NHZ
(prepared by the method of Example 4) (350 mg) was dissolved in MeOH (20 ml) and added to a suspension of 10% palladium on charcoal (100 mg) in water (10 ml). Hydrogen was bubbled through for 4 hours at 22° C. The catalyst was then filtered off and the solvents removed under reduced pressure. The residue was dissolved in a small amount of 1% pyridine in water and applied to SP Sephadex resin column (eluted in gradient 1% aqueous pyridine→1% aqueous pyridine acetate→5% aqueous pyridine acetate). Relevant franctions were pooled and the solvent removed by evaporation in vacuo. The product (220 mg) was freeze dried from water. Rf3B 0.45 Rf4A 0.56 $[\alpha]_{589}^{22} = +22.22°$ (c=0.98; 0.1 M HCl).

EXAMPLE 7

L-Tyrosyl-D-alanylglycyl-N-methyl-L-phenylalanine-3-trimethylammoniumpropylamide acetate (1)

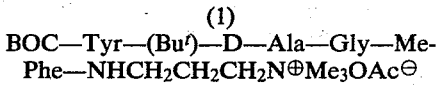

BOC—Tyr(Bu$^t$)—D—Ala—Gly—MePheNHCH₂CH₂CH₂NMe₂ (640 mg) was dissolved in ethanol, (5 ml). Methyl iodide (572 mg) was added and the solution stirred at room temperature for 48 hours. The solution was evaporated, the residue dissolved in ethyl acetate and applied to a column of silica gel (40×2 cm) and eluted with ethyl acetate:pyridine:acetic acid:water 90:20:6:11. The fractions containing the desired compound were combined and evaporated down to afford a solid (320 mg). Rf3A 0.17 Rf3B 0.74 Rf4A 0.47.

(2)

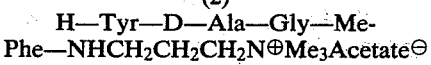

The above protected tetrapeptide (300 mg) was dissolved in ethyl acetate (10 ml) and a solution of HCl in ethyl acetate (3.9 M, 4 ml) added to the stirred solution. After 1 hour the solution was evaporated and the residue dissolved in water and applied to CM 52 cellulose column (35×3 cm) and eluted with linear concentration gradient of 0.05% aqueous pyridine to 1% aqueous pyridine-acetate. The fractions containing the desired compound were combined, evaporated, and the residue lyophilised from water to yield the desired product (110 mg) as a white solid. Rf3B 0.17, Rf4A 0.13 Rf5B 0.05 $[\alpha]_{589}^{22} = -37.75°$ (c=0.5, DMF).

EXAMPLE 8

L-Tyrosyl-D-methionylglycyl-N-methyl-L-phenylalanine-2-dimethylaminoethylamide-N-oxide (1) BOC—Gly—MePhe—NH(CH₂)₂N(O)Me₂

BOC—Gly—MePhe—NH(CH₂)₂NMe₂ (2.64 g) was dissolved in methanol (200 ml) and meta-chloroperbenzoic acid (1.23 g) was added. The reaction mixture was stirred at 22° for 2 hours then allowed to stand at 5° for 18 hours.

The solvent was removed under reduced pressure and the residue dissolved in ethyl acetate (150 ml) and the solution was washed with saturated aqueous sodium bicarbonate solution (2×30 ml), dried (Na₂SO₄) and evaporated to give the N-oxide (1.9 g) Rf3A 0.76, Rf4A 0.64.

(2) HCl.H—Gly—MePhe—NH(CH₂)₂N(O)Me₂

The above protected N-oxide (1.8 g) was dissolved in ethyl acetate (10 ml) and acetic acid (10 ml) added to the solution. A solution of hydrogen chloride in ethyl acetate (3.9 M, 12 ml) was added and the mixture stirred at 21° for 30 minutes. The solvent was removed in vacuo and the resulting solid triturated with anhydrous diethyl ether (2×40 ml). The N-oxide hydrochloride (1.5 g) was collected by filtration. Rf4A 0.40.

(3)

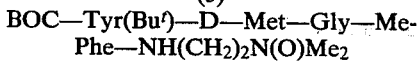

BOC—Tyr(Bu$^t$)—D—Met—OH (1.8 g) was dissolved in dry DMF (10 ml) and HONSu (0.87 g) was added to the solution.

HCl.H—Gly—MePhe—NH(CH$_2$)$_2$N(O)Me$_2$ (1.5 g) and NMM (0.84 ml) were dissolved in dry DMF (20 ml).

The two solutions were mixed, cooled to −10° and DCCI (0.87 g) was added. The mixture was stirred at −10° for 2 hours then at 20° for 18 hours.

The reaction mixture was filtered and the clear solution evaporated in vacuo. The resulting gum was partitioned between ethyl acetate (60 ml) and water (10 ml) and the organic phase washed with 10% aqueous sodium bicarbonate solution (1×10 ml) and then extracted with 10% aqueous citric acid solution (5×15 ml). The pH of the aqueous phase was then adjusted to 7 using solid sodium bicarbonate, and extracted into ethyl acetate (3×40 ml). The organic phase was dried (Na$_2$SO$_4$) and evaporated to yield a gum (1.35 g). Rf3A 0.48

(4)
HCl.H—Tyr—D—Met—Gly—MePhe—NH(CH$_2$)$_2$-N(O)Me$_2$

BOC—Tyr(Bu$^t$)—D—Met—Gly—MePhe—NH(CH$_2$)$_2$N(O)Me$_2$ (1.11 g) was dissolved in a mixture of trifluoroacetic acid (36 ml) and water (4 ml) containing anisole (0.2 ml). The mixture was stirred for 30 minutes at 22° prior to evaporation in vacuo. The product was purified by silica gel chromatography using a gradient system (solvent systems 3A→2B) as eluant. The material from the silica gel column was applied to a carboxymethyl cellulose column eluted with a gradient from 0.1% aqueous pyridine to 1.5% aqueous pyridine acetate.

Pertinent fractions were pooled, evaporated and the residue freeze dried repeatedly from dilute HCl, to give the desired hydrochloride (341 mg). Rf3B 0.31 Rf4A 0.44 Rf5B 0.19 $[\alpha]_{589}^{19} = +29.30°$ (c=0.99, 0.1 N HCl).

EXAMPLE 9

L-Tyrosyl-D-methionyl(sulphoxide)glycyl-N-methyl-L-phenylalanine-2-dimethylaminoethylamide-N-oxide HCl.H—Tyr—D—Met—Gly—MePhe—NH(CH$_2$)$_2$-N(O)Me$_2$ (418 mg) was dissolved in ethanol (150 ml) and 100 vol hydrogen peroxide (1.46 ml) was added. The solution was stirred at 21° for 24 hours, after which the solvent was removed under reduced pressure and the resulting material purified by chromatography on CM Cellulose using gradient elution from 0.1% aqueous pyridine to 1.5% aqueous pyridine acetate.

The material from the column was freeze dried repeatedly from HCl, to give the desired hydrochloride (354 ml). Rf3B 0.32 Rf4A 0.43 Rf5B 0.32 $[\alpha]_D^{20} = +9.16°$ (c=1.05, 0.1 N HCl).

The Table sets out details of further compounds of Formula I prepared by the methods of the above Examples.

| Ex. | Compound | [α] | Rf | Method |
|---|---|---|---|---|
| 10 | H—Tyr—D—Ala—Gly—Phe—NH(CH$_2$)$_3$CONH$_2$ | $[\alpha]_D^{19.5} = +52.8$ (c = 1.04, 0.1N HCl) | 3C 0.35 4A 0.60 | 1 |
| 11 | H—Tyr—D—Ala—Gly—MePhe—NH(CH$_2$)$_3$CONMe$_2$ | $[\alpha]_D^{20} = -43.3$ (c = 1, DMF) | 1F 0.15 3A 0.17 4A 0.53 | 2 |
| 12 | H—Tyr—D—Ala—Gly—MePhe—NH(CH$_2$)$_2$NHCOCH$_3$ | $[\alpha]_D^{19.5} = +26.1$ (c = 1.0, 0.1N HCl) | 3A 0.19 3B 0.85 | 2 |
| 13 | H—Try—D—Ala—Gly—MePhe—NH(CH$_2$)$_3$CO$_2$Me | $[\alpha]_D^{19.5} = +23.0$ (c = 0.86, 0.1N HCl) | 3A 0.41 3B 0.62 | 2 |
| 14 | H—Tyr—D—Ala—Gly—MePhe—NH(CH$_2$)$_3$CO$_2$H | $[\alpha]_D^{19.5} = +25.5$ (c = 1.07, 0.1N HCl) | 3A 0.22 3B 0.49 | a |
| 15 | H—Tyr—D—Ala—Gly—MePhe—NH(CH$_2$)$_3$CONH$_2$ | $[\alpha]_D^{19.5} = +23.1$ (c = 1.0, 0.1N HCl) | 3A 0.31 3B 0.32 | b |
| 16 | H—Tyr—D—Ala—Gly—MePhe—NH(CH$_2$)$_3$NHCOCH$_3$ | $[\alpha]_D^{20} = +4.8$ (c = 1, DMF) | 3B 0.76 4A 0.64 7B 0.24 | 4 |
| 17 | H—Tyr—D—Ala—Gly—MePhe—NH(CH$_2$)$_3$CONHMe | $[\alpha]_D^{22} = +17.4$ (c = 0.52, 0.1N HCl) | 4A 0.60 7B 0.22 | 2 |
| 18 | 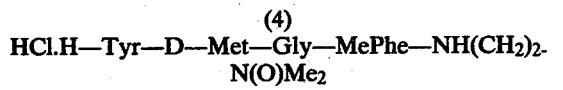 H—Tyr—D—Ala—Gly—Phe—N⌒S→O | $[\alpha]_D^{18.5} = +59.1$ (c = 0.44, 0.1N HCl) | 3A 0.17 5B 0.36 7C 0.05 | 5 |
| 19 | H—Tyr—D—Ala—Gly—MePhe—NH(CH$_2$)$_3$CONMePh | $[\alpha]_D^{24} = +16.2$ (c = 0.54, 0.1N HCl) | 3A 0.36 4A 0.69 | 2 |
| 20 | H—Tyr—D—Ala—Gly—MePhe—NH(CH$_2$)$_4$CONMe$_2$ | $[\alpha]_D^{24} = +17.3$ (c = 0.52, 0.1N HCl) | 3A 0.60 7B 0.11 | 2 |
| 21 | H—Tyr—D—Ala—Gly—MePheNH(CH$_2$)$_2$CONMe$_2$ | $[\alpha]_D^{24} = +17.0$ (c = 0.50, 0.1N HCl) | 4A 0.58 7B 0.22 | 4 |
| 22 | H—Tyr—D—Ala—Gly—MePhe—NH(CH$_2$)$_2$N(O)Me$_2$ | $[\alpha]_D^{20} = -42.1$ (c = 0.50, DMF) | 3A 0.05 3B 0.54 4A 0.55 | 3 |
| 23 | H—Tyr—D—Ala—Gly—MePhe—N(Me)(CH$_2$)$_3$CONMe$_2$ | $[\alpha]_D^{24} = +2.2$ (c = 0.51, 0.1 NHCl) | 3A 0.51 7B 0.42 | 4 |
| 24 | H—Tyr—D—Ala—Gly—Phe—N(piperazine)N→O | $[\alpha]_D^{24} = +11.9$ (c = 0.57, H$_2$O) | 3A 0.48 4A 0.40 | 1 & 3 |
| 25 | H—Tyr—D—Ala—Gly—MePhe—N(Me, CH$_2$CH$_2$CHMe$_2$)(CH$_2$CH$_2$NMe$_2$) | $[\alpha]_D^{24} = -2.0$ (c = 0.50, 0.1N HCl) | 3B 0.36 4A 0.45 | 4 |

-continued

| Ex. | Compound | [α] | Rf | Method |
|---|---|---|---|---|
| 26 | H—Tyr—D—Ala—Gly—MePhe—N(CH$_2$CH$_2$CHMe$_2$)(CH$_2$CH$_2$N(O)Me$_2$) | $[\alpha]_D^{24} = -0.8$ (c = 0.50, 0.1N HCl) | 3A 0.22  4A 0.35 | 3 |
| 27 | H—Tyr—D—Ala—Gly—MePheNH(CH$_2$)$_3$NMe$_2$ | $[\alpha]_D^{24} = -42$ (c = 1, DMF) | 3B 0.44  4A 0.48 | 6 |
| 28 | H—Tyr—D—Ala—Gly—Phe—N(piperazine-N(O)-Ph) | $[\alpha]_D^{20} = -68.2$ (c = 1, DMF) | 3A 0.19  3B 0.69  4A 0.58 | 1 & 3 |
| 29 | H—Tyr—D—Ala—Gly—MePheNH(CH$_2$)$_2$NMePh | $[\alpha]_D^{20} = -46.8$ (C = 1, DMF) | 3A 0.35  4A 0.70  7B 0.39 | 4 |
| 30 | H—Tyr—D—Ala—Gly—MePheNH(CH$_2$)$_2$N(O)MePh | $[\alpha]_D^{20} = -40.2$ (c = 1, DMF) | 3B 0.63  4A 0.53  7A 0.12 | 3 |
| 31 | MeTyr—D—Ala—Gly—MePheNH(CH$_2$)$_2$NMe$_2$ | $[\alpha]_D^{20} = +21.1$ (c = 1, 0.1N HCl) | 3B 0.33  4A 0.25  5B 0.12 | 4 |
| 32 | MeTyr—D—Ala—Gly—MePheNH(CH$_2$)$_2$N(O)Me$_2$ | $[\alpha]_D^{20} = +25.5$ (c = 0.94, 0.1N HCl) | 3B 0.36  4A 0.35  5B 0.15 | 3 |
| 33 | H—Tyr—D—Nva—Gly—MePheNH(CH$_2$)$_2$NMe$_2$ | $[\alpha]_D^{20} = +28.5$ (c = 0.91, 0.1N HCl) | 3B 0.39  4A 0.38  5B 0.18 | 4 |
| 34 | H—Tyr—D—Nva—Gly—MePheNH(CH$_2$)$_2$N(O)Me$_2$ | $[\alpha]_D^{20} = +26.2$ (c = 0.91, 0.1N HCl) | 3B 0.41  4A 0.48  5B 0.25 | 3 |
| 35 | H—Tyr—D—Ser—Gly—MePheNH(CH$_2$)$_2$NMe$_2$ | $[\alpha]_D^{19} = +5.4$ (c = 0.97, 0.1N HCl) | 3B 0.23  4A 0.21  5B 0.12 | 4 |
| 36 | H—Tyr—D—Ser—Gly—MePheNH(CH$_2$)$_2$N(O)Me$_2$ | $[\alpha]_D^{19} = +4.2$ (c = 1, 0.1N HCl) | 3B 0.22  4A 0.30  5B 0.17 | 3 |
| 37 | H—Tyr—D—Met—Gly—MePheNH(CH$_2$)$_2$NMe$_2$ | $[\alpha]_D^{19} = +30.0$ (c = 0.93, 0.1N HCl) | 3B 0.31  4A 0.27  5B 0.16 | 4 |
| 38 | H—Tyr—D—Ala—Gly—MePheNH(CH$_2$)$_2$NHCO$_2$C$_2$H$_5$ | $[\alpha]_D^{20} = +25.3$ (c = 0.91, 0.1N HCl) | 3A 0.35  4B 0.72  7B 0.34 | 4 |
| 39 | H—Tyr—D—Ala—Gly—MePheNH(CH$_2$)$_2$NHCONH$_2$ | $[\alpha]_D^{23} = +23.5$ (c = 0.97, 0.1N HCl) | 3A 0.12  4A 0.62  7A 0.50 | 4 |
| 40 | H—Tyr—D—Ala—Gly—MePheNH(CH$_2$)$_2$OCONH$_2$ | $[\alpha]_D^{19} = +25.7$ (c = 0.97, 0.1N HCl) | 3A 0.13  3B 0.54  7A 0.49 | 4 |
| 41 | H—Tyr—D—Ala—Gly—MePheNH(CH$_2$)$_2$NHCONMe$_2$ | $[\alpha]_D^{23} = +24.8$ (c = 0.96, 0.1N HCl) | 3A 0.15  3B 0.57  7A 0.33 | 4 |
| 42 | H—Tyr—D—Ala—Gly—MePheN(CH$_2$CH$_2$Ph)((CH$_2$)$_2$NMe$_2$) | $[\alpha]_D^{22} = -5.4$ (c = 0.58, 0.1N HCl) | 3A 0.85  7B 0.46 | 4 |
| 43 | H—Tyr—D—Ala—Gly—MePheN(CH$_2$CH$_2$Ph)((CH$_2$)$_2$N(O)Me$_2$) | $[\alpha]_D^{22} = -5.0$ (c = 0.58, 0.1N HCl) | 3A 0.17  3B 0.67 | 3 |
| 44 | H—Tyr—D—Ala—Gly—MePheNHC(CH$_2$CH(CH$_3$)$_2$)(H)(CH$_2$NMe$_2$) | $[\alpha]_D^{19} = -53.3$ (c = 1.25, DMF) | 3B 0.47  4A 0.55  5B 0.41 | 4 |
| 45 | H—Tyr—D—Ala—Gly—MePheNHC(CH$_2$CHMe$_2$)(H)(CH$_2$N(O)Me$_2$) | | 3B 0.48  4A 0.56  5B 0.46 | 3 |
| 46 | H—Tyr—D—Ala—Gly—MePhe—NHCH$_2$CH$_2$NMeCH$_2$CH$_2$CHMe$_2$ | $[\alpha]_D^{19} = +23.8$ (c = 0.93, 0.1N HCl) | 3B 0.52  4A 0.57  5B 0.36 | 4 |
| 47 | H—Tyr—D—Ala—Gly—MePhe—NHCH$_2$CH$_2$N(O)MeCH$_2$CH$_2$CHMe$_2$ | | 3A 0.40  3B 0.60  4A 0.54 | 3 |
| 48 | H—Tyr—D—Ala—Gly—MePhe—NHCH$_2$CH$_2$NHCO$_2$CH$_2$Ph | $[\alpha]_D^{19.5} = +18.3$ (c = 0.51, 0.1N HCl) | 3D 0.76  4A 0.76 | 4 |

-continued
| Ex. | Compound | [α] | Rf | Method |
|---|---|---|---|---|
| 49 | H—Tyr—D—Ala—Gly—MePhe—NHCH$_2$CH$_2$CH$_2$NHCO$_2$CH$_2$Ph | $[α]_D^{19.5} = -38.0$ (c = 1, DMF) | 7B 0.33<br>3A 0.32<br>4A 0.73<br>7B 0.45 | 4 |
a = hydrolysis of Ex. 11
b = ammonalysis of Ex. 11
The following are other typical compounds of the invention:
H—Tyr—D—Ala—Gly—MePhe(p-Cl)—NHCH$_2$CH$_2$N(O)Me$_2$.
H—Tyr—D—Ala—Gly—Phe(p-Cl)—NHCH$_2$CH$_2$N(O)Me$_2$.
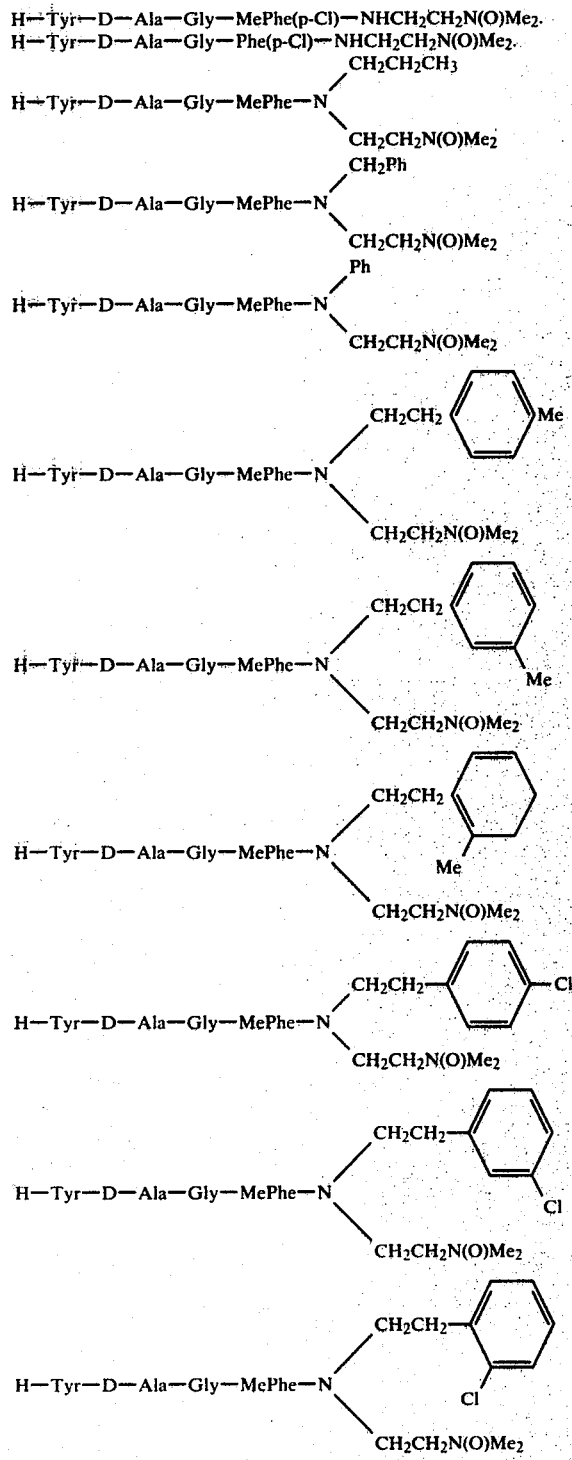

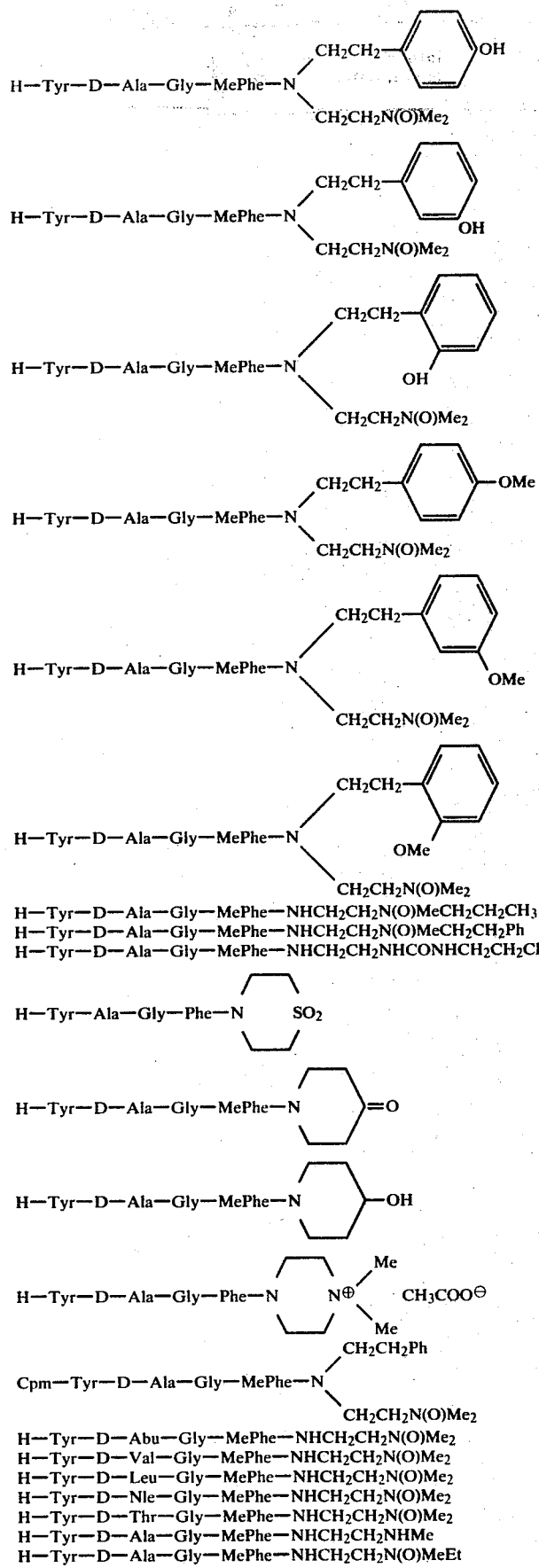
H—Tyr—D—Ala—Gly—MePhe—NHCH₂CH₂N(O)MeCH₂CH₂CH₃
H—Tyr—D—Ala—Gly—MePhe—NHCH₂CH₂N(O)MeCH₂CH₂Ph
H—Tyr—D—Ala—Gly—MePhe—NHCH₂CH₂NHCONHCH₂CH₂CH₃

Cpm—Tyr—D—Ala—Gly—MePhe—N(CH₂CH₂Ph)(CH₂CH₂N(O)Me₂)
H—Tyr—D—Abu—Gly—MePhe—NHCH₂CH₂N(O)Me₂
H—Tyr—D—Val—Gly—MePhe—NHCH₂CH₂N(O)Me₂
H—Tyr—D—Leu—Gly—MePhe—NHCH₂CH₂N(O)Me₂
H—Tyr—D—Nle—Gly—MePhe—NHCH₂CH₂N(O)Me₂
H—Tyr—D—Thr—Gly—MePhe—NHCH₂CH₂N(O)Me₂
H—Tyr—D—Ala—Gly—MePhe—NHCH₂CH₂NHMe
H—Tyr—D—Ala—Gly—MePhe—NHCH₂CH₂N(O)MeEt

H—Tyr—D—Ala—Gly—MePhe—NHCH₂CH₂N(O)Et₂
H—Tyr—D—Ala—Gly—MePhe—NHCH₂CH₂NMeEt
H—Tyr—D—Ala—Gly—MePHe—NHCH₂CH₂NEt₂.

The starting amines of formula HNR⁸Rˣ used in the preparation of the above Examples, when not commercially available may be prepared by methods known per se or in the case of particular amines as follows:

EXAMPLE A

N-Isoamyl-N',N'-dimethylethylene diamine (1) Me₂CHCH₂CONHCH₂CH₂NH₂

Isovaleroyl chloride (5 g, 38 mmole) in dichloromethane was added dropwise to a stirred solution of N,N-dimethylethylene diamine (3,38 g, 38 mmole) and NMM (7.75 g, 76.7 mmoles) in CH₂Cl₂ at 0° C. The reaction mixture was stirred at room temperature for four hours when the solvent was evaporated. The residue was taken up in 5 M NaOH (50 ml) and extracted with ethyl acetate (2×100 ml). The ethyl acetate was washed with a saturated aqueous solution of sodium chloride, dried (Na₂SO₄) and evaporated. The residue was dissolved in diethyl ether and 5 M HCl in ethyl acetate (10 ml) added. The resulting solid was filtered, washed with diethyl ether (5+10 ml) and dried under high vacuum.
Yield=5.43 g, Rf3A 0.40.

(2) Me₂CHCH₂CH₂NHCH₂CH₂NH₂

A solution of the above amide (5 g) in dry THF (50 ml) was added dropwise to a stirred suspension of LiAlH₄ (2 g) in dry THF (20 ml) at room temperature. The reaction mixture was then refluxed for 4 hours when t.l.c. showed absence of starting material. A saturated aqueous solution of sodium sulphate was added to quench excess LiAlH₄. The resulting suspension was filtered and the filtrate acidified with 4M HCl (10 ml). The solvent was evaporated to leave a white solid which was triturated with diethyl ether, filtered and dried.
Yield=5.51 g.

EXAMPLE B

N-Phenethyl-N',N'-dimethylethylene diamine (1) Ph CH₂CONHCH₂CH₂NH₂.HCl

This was prepared in a similar manner as described in Example A(1) by coupling phenacetyl chloride (1.0 g, 6.47 mmoles) with N,N-dimethylethylene diamine 0.42 g, 6.47 mmoles) in the presence of NMM.
Yield=1.38 g, RF3A=0.30.

(2) PhCH₂CH₂NHCH₂CH₂NH₂.HCl

This was prepared by LiAlH₄ reduction of the amide above (10 g) as described for Example A(2). An impure product (12 g) was obtained which was purified by silica gel column chromatography eluting with solvent system 3A.
Yield=4.5 g, Rf3B=0.31.

EXAMPLE C

N-(2-Aminoethyl)-N',N'-dimethylurea (1) PhCH₂OCONHCH₂CH₂NHCONMe₂

A solution of dimethylcarbamoyl chloride (1.39 g) in diethyl ether (15 ml) was added dropwise to a stirred solution of NMM (1.57 g) and 2-benzyloxycarbonylaminoethylamine (3.02 g) in diethyl ether (110 ml). The mixture was stirred for four hours and allowed to stand for two days. After evaporation of the ether the residual solid was partitioned between 10% aqueous citric acid and ethyl acetate. The ethyl acetate extracts were washed with 10% aqueous citric acid, saturated sodium bicarbonate solution, and saturated sodium chloride solution, and then dried (Na₂SO₄) and evaporated to give a solid (1.7 g). A sample crystallised from ethyl acetate/patroleum ether (bp. 60°-80°) m.p. 81°-82°.

(2) H₂NCH₂CH₂NHCONMe₂

The above N-benzyloxycarbonyl compound (1.06 g) was hydrogenlysed over 10% Pd/C (100 mg) in ethanol (30 ml) containing 2N aqueous hydrochloric acid (2.1 ml) for 1½ hours. Filtration and evaporation of the filtrate yielded the desired compound as the hydrochloride which was used without purification.

EXAMPLE D

N-Isoamyl-N-methylethylenediamine (1) BOC—Gly—N(Me)CH₂CH₂CHMe₂

BOC—Gly—OH (17.5 g, 0.1 mole) was dissolved in dry CH₂Cl₂ (100 ml) when NMM (10.1 g, 0.1 mole) and IBCF (13.7 g, 0.1 mole) were added at −15° C. After two minutes N-methylisoamylamine hydrochloride (13.7 g, 0.1 mole) and NMM (10.1 g) were added. The reaction mixture was stirred at −15° C. for 1½ hours and at room temperature overnight. The solvent was evaporated and the oil dissolved in ethyl acetate, extracted with saturated sodium bicarbonate (2×100 ml), 10% aqueous citric acid (2×100 ml) washed with water until neutral, dried (Na₂SO₄) and evaporated. An oil was obtained.
Yield=27 g (quantilative), Rf7D=0.79.

(2) H₂NCH₂CH₂N(Me)CH₂CH₂CHMe₂

BOC—Gly—N(Me)CH₂CH₂CHMe₂ (12 g) was dissolved in 90% TFA aqueous trifluoroacetic acid (H₂O:CH₃COOH 1:9, 35 ml). After two minutes the solvent was evaporated to leave an oil. The oil was dissolved in 50 ml of freshly dried THF and added to diborane in THF (1M, 150 ml) under an atmosphere of nitrogen at −20° C. The temperature was allowed to reach room temperature and the reaction mixture stirred overnight. Methanol (100 ml) was carefully added to destroy the excess diborane and solvent evaporated to yield an oil. The oil was then treated with 6 M HCl (50 ml). The reaction mixture was refluxed for 3 hours and evaporated down to an oil. This oil was further treated with 2M NaOH for 1 hour, acidified and evaporated. The oil so obtained was purified by silica gel column chromatography (2.5 cm×80 cm) with solvent system 3A to yield the desired diamine.
Yield=4.4 g, Rf3A=0.20.

EXAMPLE E

Dimethyl(2-amino-4-methylpentyl)amine

(1) BOC—Leu—NMe₂

BOC—Leu—OH (4.62 g, 20 mM) was dissolved in CH₂Cl₂ and the solution cooled to −20°. NMM (2.25 ml, 20 mM) and chlorodiphenylphosphate oxide (6.0 g, 20 mM) were added, followed after 15 minutes by dimethylamine (5.6 g, 125 mM). After 3 hours at 20° the solution was evaporated and the residue partitioned between ethyl acetate and water (50 mls each). The organic phase was washed with 10% aqueous citric acid, aqueous sodium bicarbonate and saturated brine, dried (Na₂SO₄) and evaporated to yield the desired amide (5.15 g).

(2) Me₂NCH₂CH(NH₂)CH₂CHMe₂

BOC—Leu—NMe₂ (1.3 g, 5 mM) was dissolved in aqueous trifluoroacetic acid (H₂O:CH₃COOH 9:1, 20 ml) and the solution stirred for 1 hour. The solvent was then evaporated and the residue dissolved in dry THF. The stirred solution was cooled to −20° under nitrogen and a solution of diborane in THF (1 M, 30 ml) added. After 5 hours at room temperature, methanol (10 ml) was added and the solution stirred for 12 hours before evaporation. The residue was dissolved in aqueous HCl (2M, 15 ml) and stirred for a further 12 hours before evaporation. The residue was purified by chromatography in silica gel (system 7C→7B). Pertinent fractions were pooled and evaporated to yield the desired diamine as an oil (800 mp) which crystallised on standing.

In the above mentioned test method of Kosterlitz et al male or female guinea pigs (Duncan Hartley strain) are killed by a blow on the head and a portion of the ileum removed and set up in an isolated organ bath of 50 ml volume. A 'twitch' response is produced by low frequency (0.1 Hz) stimulation with 0.5 msec rectilinear pulses. A test compound is dissolved in distilled water to produce a stock solution of concentration 1 mg/ml. Serial dilutions are carried out using Krebs solution to produce concentrations of 10 µg, 1 µg and 0.1 µg/ml. The compound is tested by adding between 0.1–0.3 ml of the solutions to the organ bath. A dose response curve is then drawn and compared with that for Met enkephalin.

In the rat tail flick test hot water (maintained at 55°±1° C.) is used as the nociceptive stimulus.

The following are data obtained with compounds of the invention when tested by the guinea pig ileum (G.P.I., activity compared with Met enkephalin), Hendershot et al (H & F) and rat tail pressure (R.T.F) tests.

| Exxample No. | G.P.I. Potency (X Met enkephalin) | H & F ED₅₀ mg/Kg i.v. | R.T.F. ED₅₀ mg/Kg i.v. |
|---|---|---|---|
| 1 | 2.6 | 0.01 | |
| 2 | 7.2 | 0.28 | 2.0 |
| 3 | 4.1 | 0.00003 | 1.8 |
| 4 | 8.5 | 0.003 | 1.4 |
| 22 | 6.5 | 0.08 ng/Kg | 0.32 |
| 6 | 13.0 | 0.028 | 0.37 |
| 19 | 23.2 | 0.24 | |
| Morphine | ≈1.0 | 0.07 | 2.2 |

The pharmaceutical compositions may be, for example, in a form suitable for parenteral administration such as sterile injectable aqueous or oily solutions or suspensions. The parenteral dosage forms suitable for intraveneous intramuscular or subcutaneous administration contain from 0.1 to 50 mg/ml of a compound of the invention (or an equivalent amount of a pharmaceutically acceptable salt). Dose levels will generally, for the relief of pain, be in the range of 0.1 to 100 mg depending upon the route of injection.

What is claimed is:

1. A compound of the formula:

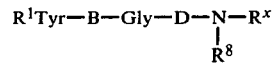

wherein
R¹ is hydrogen, methyl, allyl, dimethylallyl, propargyl, cyclopropylmethyl, cyclobutylmethyl or phenethyl;
B is the group

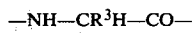

in which R³ is alkyl C₁₋₆ or C_qH_{2q}YC_rH_{2r+1} (where q is 1-2, r is 0-1 and Y is O, S, SO or SO₂); the group having the D-configuration;
D is the group

in which
R⁵ is hydrogen or methyl;
R⁶ Ar-alkyl C₁₋₃;
the group having the L-configuration;
R⁸ is hydrogen, alkyl C₁₋₅, Ar or Ar-alkyl C₁₋₂;
Rˣ is a group (CH₂)_s—X where s is 2-4 and X is NHR⁹, N⊕R¹¹R¹²R¹³, NR⁹COR¹¹, NR⁹COOR¹¹, NR⁹CONH₂, NR⁹CONR¹⁰R¹¹, N(O)_nR¹¹R¹², COOR⁹, CONR⁹R¹⁰, or OCONR⁹R¹⁰ (where R⁹ is hydrogen, alkyl C₁₋₃, Ar or ArCH₂;
R¹⁰ is hydrogen or alkyl C₁₋₃; R¹¹ is alkyl C₁₋₃, Ar or ArCH₂; R¹² is alkyl C₁₋₃; R¹³ is alkyl C₁₋₃; and n is 0 or 1);
or the group

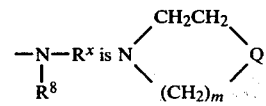

where m is 1-3 and Q is SO, SO₂, CO CHOH, N⊕MeR¹¹ or N(O)R¹¹;
Ar is phenyl or phenyl substituted by chlorine, methyl, hydroxy or methoxy; and their acid addition salts.

2. A compound of the formula

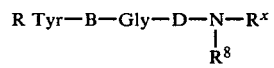

wherein
R¹ is hydrogen, methyl, allyl, dimethylallyl, propargyl, cyclopropylmethyl, cyclobutylmethyl or phenethyl;
B is the group

in which $R^3$ is alkyl $C_{1-6}$ or $C_qH_{2q}YC_rH_{2r+1}$ (where q is 1-2, r is 0-1 and Y is O, S, SO or $SO_2$), the group having the D-configuration;

D is the group

—$NR^5$—$CR^6H$—CO— in which $R^5$ is hydrogen or methyl;

$R^6$ is Ar-alkyl $C_{1-3}$, the group having the L-configuration;

$R^8$ is hydrogen or alkyl $C_{1-5}$;

$R^x$ is a group $(CH_2)_s$—X where s is 2-4 and X is $NHR^9$, $NR^9COR^{11}$, $NR^9CONH_2$, $NR^9CONR^{10}R^{11}$, $N(O)_nR^{11}R^{12}$, $COOR^9$, $CONR^9R^{10}$, $NR^9COOR^{11}$ or $OCONR^9R^{10}$ (where $R^9$ is hydrogen or alkyl $C_{1-3}$;

$R^{10}$ is hydrogen or alkyl $C_{1-3}$; $R^{11}$ is alkyl $C_{1-3}$;

$R^{12}$ is alkyl $C_{1-3}$ and n is 0 or 1);

Ar is phenyl or phenyl substituted by chlorine, methyl, hydroxy or methoxy; and their acid addition salts.

3. A compound as claimed in claim 1 or claim 2 wherein B is D-alanine, D-α-aminobutyric acid, D-valine, D-norvaline, D-leucine, D-norleucine, D-serine, D-threonine, D-methionine or D-methionine sulphoxide.

4. A compound as claimed in claim 1 or claim 2 wherein D is L-phenylalanine or N-methyl-L-phenylalanine.

5. A compound of claim 1 which is L-tyrosyl-D-alanylglycyl-L-phenylalanine-2-acetamidoethylamide.

6. A compound of claim 1 which is L-tyrosyl-D-alanylglycyl-N-methyl-L-phenylalanine-3-dimethylaminopropylamide.

7. A compound of claim 1 which is L-tyrosyl-D-alanylglycyl-N-methyl-L-phenylalanine-3-dimethylaminopropylamide-N-oxide.

8. A compound of claim 1 which is L-tyrosyl-D-alanylglycyl-N-methyl-L-phenylalanine-2-dimethylaminoethylamide.

9. A compound of claim 1 which is L-tyrosyl-D-alanyglycyl-N-methyl-L-phenylalanine-2-dimethylaminoethylamide-N-oxide.

10. A compound of claim 1 which is L-tyrosyl-D-alanylglycyl-N-methyl-L-phenylalanine-2-aminoethylamide.

11. A compound of claim 1 which is L-tyrosyl-D-alanylglycyl-N-methyl-L-phenylalanine-γ-aminobutyric-N-methyl-N-phenylamide.

12. A compound of claim 1 which is selected from the group consisting of

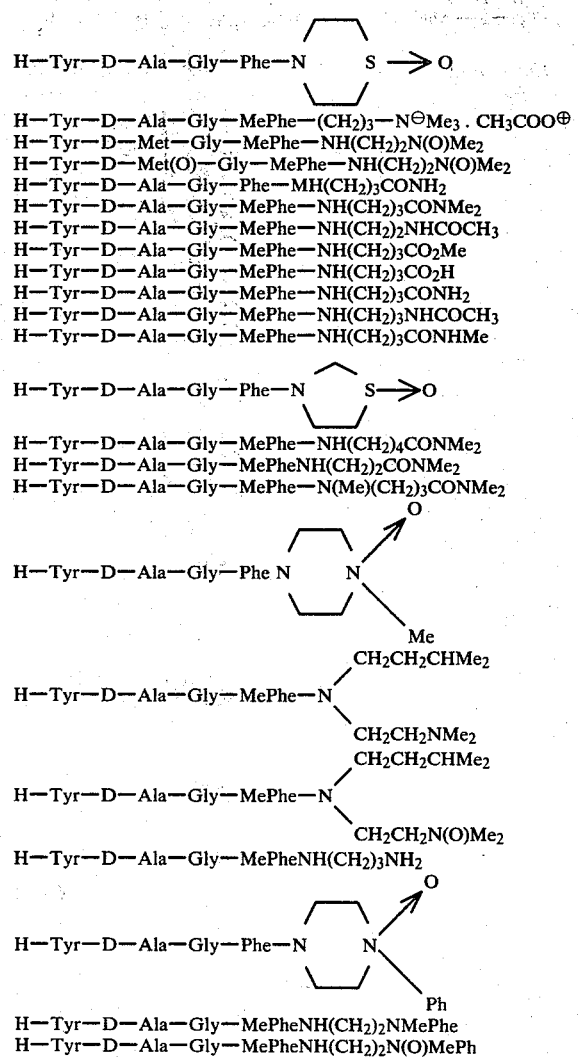

MeTyr—D—Ala—Gly—MePheNH(CH₂)₂NMe₂
MeTyr—D—Ala—Gly—MePheNH(CH₂)₂N(O)Me₂
H—Tyr—D—Nva—Gly—MePheNH(CH₂)₂NMe₂
H—Tyr—D—Nva—Gly—MePheNH(CH₂)₂N(O)Me₂
H—Tyr—D—Ser—Gly—MePheNH(CH₂)₂NMe₂
H—Tyr—D—Ser—Gly—MePheNH(CH₂)₂N(O)Me₂
H—Tyr—D—Met—Gly—MePheNH(CH₂)₂NMe₂
H—Tyr—D—Ala—Gly—MePheNH(CH₂)₂NHCO₂C₂H₅
H—Tyr—D—Ala—Gly—MePheNH(CH₂)₂NHCONH₂
H—Tyr—D—Ala—Gly—MePheNH(CH₂)₂OCONH₂
H—Tyr—D—Ala—Gly—MePheNH(CH₂)₂NHCONMe₂

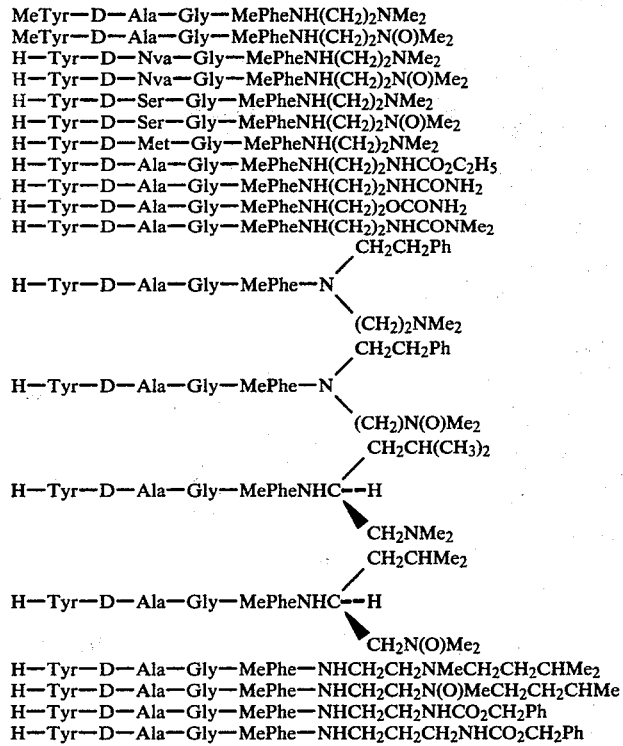

H—Tyr—D—Ala—Gly—MePhe—NHCH₂CH₂NMeCH₂CH₂CHMe₂
H—Tyr—D—Ala—Gly—MePhe—NHCH₂CH₂N(O)MeCH₂CH₂CHMe
H—Tyr—D—Ala—Gly—MePhe—NHCH₂CH₂NHCO₂CH₂Ph
H—Tyr—D—Ala—Gly—MePhe—NHCH₂CH₂CH₂NHCO₂CH₂Ph

13. A pharmaceutical composition which comprises an effective amount of at least one compound as claimed in claim 1 or a pharmaceutically acceptable salt thereof together with a pharmaceutically acceptable diluent or carrier.

14. A compound as claimed in claim 1 or claim 2 where B is D-alanine, D-α-aminobutyric acid, D-valine, D-norvaline, D-leucine, D-norleucine, D-serine, D-threonine, D-methionine or D-methionine sulphoxide and D is L-phenylalanine or N-methyl-L-phenylalanine.

* * * * *